(12) United States Patent
Plevnik et al.

(10) Patent No.: US 8,834,360 B2
(45) Date of Patent: Sep. 16, 2014

(54) LARYNGOSCOPE

(75) Inventors: Marko Plevnik, London (GB); Brian Gough, Middlesex (GB)

(73) Assignee: Indian Ocean Medical Inc., Mahe (SC)

( * ) Notice: Subject to any disclaimer, the term of this patent is extended or adjusted under 35 U.S.C. 154(b) by 0 days.

(21) Appl. No.: 13/264,471

(22) PCT Filed: Mar. 25, 2010

(86) PCT No.: PCT/GB2010/000566
§ 371 (c)(1),
(2), (4) Date: Nov. 10, 2011

(87) PCT Pub. No.: WO2010/119237
PCT Pub. Date: Oct. 21, 2010

(65) Prior Publication Data
US 2012/0071725 A1    Mar. 22, 2012

(30) Foreign Application Priority Data

Apr. 17, 2009  (GB) .................................. 0906688.7

(51) Int. Cl.
*A61B 1/267* (2006.01)
*A61B 1/00* (2006.01)
(52) U.S. Cl.
CPC ............. *A61B 1/267* (2013.01); *A61B 1/00052* (2013.01); *A61B 1/00103* (2013.01)
USPC ..................................................... 600/188
(58) Field of Classification Search
USPC ......... 600/185, 186, 188, 190, 191, 193, 194, 600/196, 197, 199; 206/363
See application file for complete search history.

(56) References Cited

U.S. PATENT DOCUMENTS

| | | | |
|---|---|---|---|
| 3,426,749 | A | 2/1969 | Jephcott |
| 4,337,761 | A | 7/1982 | Upsher |
| 4,574,784 | A | 3/1986 | Soloway |
| 4,579,108 | A | 4/1986 | Bauman |
| 4,834,077 | A | 5/1989 | Sun |
| 5,261,392 | A | 11/1993 | Wu |
| 5,347,995 | A | 9/1994 | Slater et al. |
| 5,349,943 | A | 9/1994 | Ruiz |
| 5,381,787 | A | 1/1995 | Bullard |
| 2003/0168059 | A1 | 9/2003 | Pacey |
| 2003/0181789 | A1 | 9/2003 | Mazzei |
| 2004/0220454 | A1 | 11/2004 | Dalle et al. |

(Continued)

FOREIGN PATENT DOCUMENTS

| | | |
|---|---|---|
| CN | 2870731 Y | 1/2006 |
| CN | 201194790 Y | 2/2009 |

(Continued)

OTHER PUBLICATIONS

PCT/GB2010/000566—International Search Report and the Written Opinion of the International Searching Authority, dated Jul. 22, 2010.

(Continued)

*Primary Examiner* — Pedro Philogene
*Assistant Examiner* — David Comstock
(74) *Attorney, Agent, or Firm* — Ostrager Chong Flaherty & Broitman P.C.

(57) ABSTRACT

A laryngoscope comprising a handle, a blade holding element, a releasable blade and releasable attachment means to attach the blade to the blade holding element, and handle and a blade for such a laryngoscope.

21 Claims, 8 Drawing Sheets

(56) References Cited

U.S. PATENT DOCUMENTS

| | | |
|---|---|---|
| 2005/0240081 A1 | 10/2005 | Eliachar |
| 2007/0175482 A1 | 8/2007 | Kimmel |
| 2007/0287888 A1 | 12/2007 | Lovell |
| 2008/0064926 A1 | 3/2008 | Chen |
| 2008/0208006 A1 | 8/2008 | Farr |
| 2009/0099421 A1 | 4/2009 | Shalman et al. |
| 2009/0299146 A1 | 12/2009 | McGrath |
| 2010/0041955 A1 | 2/2010 | Grey |
| 2010/0081875 A1 | 4/2010 | Fowler |
| 2010/0198009 A1 | 8/2010 | Farr |
| 2011/0028790 A1 | 2/2011 | Farr |

FOREIGN PATENT DOCUMENTS

| | | |
|---|---|---|
| EP | 1166710 A2 | 1/2001 |
| EP | 1598001 A1 | 11/2005 |
| EP | 1640033 A1 | 3/2006 |
| FR | 2381528 A1 | 9/1978 |
| JP | 19935501967 A | 4/1994 |
| JP | 200824221 | 1/1996 |
| JP | 2000184607 | 1/2002 |
| JP | 2002000732 | 1/2002 |
| JP | 200265589 A | 3/2002 |
| JP | 2005520586 | 7/2005 |
| JP | 2006525058 A | 11/2006 |
| JP | 2006326111 | 12/2006 |
| JP | 2006326111 A | 12/2006 |
| JP | 2007117116 A | 5/2007 |
| JP | 2008119305 A | 5/2008 |
| JP | 200853551 | 9/2008 |
| JP | 2008535551 A | 9/2008 |
| JP | 2008289669 A | 12/2008 |
| JP | 2009531133 | 9/2009 |
| WO | 9014041 | 11/1990 |
| WO | 0030707 A2 | 6/2000 |
| WO | 2006102770 A1 | 10/2006 |
| WO | 2007066134 A2 | 6/2007 |
| WO | 2007126657 A1 | 11/2007 |
| WO | 2008157170 A2 | 12/2008 |
| WO | 2009027669 A2 | 3/2009 |

OTHER PUBLICATIONS

Patent Examination Report No. 1 in Application No. 2009309483, Applicant: Indian Ocean Medical Inc., IP Australia, Oct. 3, 2013.
Notification of Reason for Refusal in Japanese Patent Application No. 2011-533817, Japanese Patent Office, Jun. 18, 2013.
Notification of Reason for Refusal in Japanese Patent Application No. 2012-505216, Japanese Patent Office, Aug. 14, 2013.
Patent Examination Report No. 1 in Australian patent application No. 2010288342, dated Aug. 22, 2013.
First Office Action in China Patent Application No. 201080043321X.
Notice of Reasons for Rejection in Japanese Patent Application No. 2012-526108, dated Oct. 25, 2013.

LARYNGOSCOPE

FIELD OF THE INVENTION

This application relates to a laryngoscope and more particularly to a laryngoscope with a releasable blade.

BACKGROUND OF THE INVENTION

A laryngoscope is a device, typically comprising a handle and a blade, which is used by clinicians during tracheal intubation and that assists with intubation by allowing the clinician to visualise the path of the endotracheal tube as it passes through the glottis towards the trachea.

Typically, tracheal intubation begins with the blade inserted into the corner of the patient's mouth. The blade is shaped such that a flange will push the tongue to the left side of the oropharynx to create space in the oropharynx through which a view of the larynx will be sought. The epiglottis is visualised. The laryngoscope handle is manipulated so that the blade lifts the epiglottis directly with the blade or indirectly with the curved blade thereby exposing the laryngeal inlet in normal patients. The endotracheal tube is then advanced past the vocal cords into the trachea.

Due to the contact of the laryngoscope blade with bodily fluids, the equipment must be thoroughly sterilized between uses and sterilization procedures are time-consuming and costly. Alternatively, in order to eliminate cross-contamination between patients, the blade may be covered during use with a disposable sleeve as described in U.S. Pat. No. 5,347,995. However, the sleeve can become easily detached from the blade and prevent the clinician from properly performing the intubation. Another option is to use a detachable blade which is disposed of after each use. The proximal part of the blade is typically attached to the handle by means of pins, screws or bolts.

During intubation, the clinician will direct the laryngoscope with one hand and introduce the tracheal tube with the other and it is essential that the laryngoscope is easy to handle. In addition, the presence of protruding connecting parts can potentially injure or scratch the patient's anatomy both during intubation and removal of the laryngoscope. The removal of small parts such as bolts, pins or screws is fiddly and such small parts can easily be lost. Moreover, the connecting parts themselves may retain impurities such as blood and other bodily fluids that can harden and become increasingly difficult to remove and sterilisation becomes necessary.

It is an object of this invention to mitigate problems such as those described above.

SUMMARY OF THE INVENTION

According to a first aspect of the invention, there is provided a laryngoscope comprising a handle, a blade holding element, a releasable blade and releasable attachment means to attach the blade to the blade holding element.

The blade holding element may be pivotally attached to the handle, so that the blade may be arranged in a first operative position and a second inoperative position. Preferably, the blade is shaped so that it is releasable when in the second inoperative position. The blade may also be shaped so that it is not detachable when in the first operative position. These features ensure that the blade does not become detached during use when the clinician is performing the intubation. The invention is intended to improve the ease of connection and removal of the detachable blade.

The blade and the blade holding element may comprise mutually cooperative releasable attachment means and preferably at least one of the releasable attachment means comprises a resiliently deformable element. Most preferably, the releasable attachment means is a snap clip system.

The snap clip means may comprise at least one tooth and a corresponding groove for receiving the tooth. The blade holding element may comprise a tooth and the blade comprises a corresponding groove; or the blade may comprise a tooth and the blade holding element comprises a corresponding groove.

The use of a snap clip has the advantage that the connection mechanism does not have loose parts that can become lost when the blade is detached. In addition, it minimises the risk of injury to the patient during use.

Preferably, the blade is slidable onto the blade holding element. The blade may be made partially or wholly of a flexible thermoplastic or metal material.

The laryngoscope may further comprise a light source and/or vizualisation means in order to enable the clinician to clearly view the laryngeal inlet of the patient.

According to a second aspect of the invention, there is provided a blade for use with a laryngoscope as described above.

According to a third aspect of the invention, there is provided a handle for use with a laryngoscope as described above.

The invention will be further described with reference to the drawings, in which:

DESCRIPTION OF PREFERRED EMBODIMENTS

In this application, the terms "distal part" and "proximal part" are used relative to the medical professional, i.e. the "distal part" is used to describe the part of the device that is inserted first into the patient.

Figure 1:
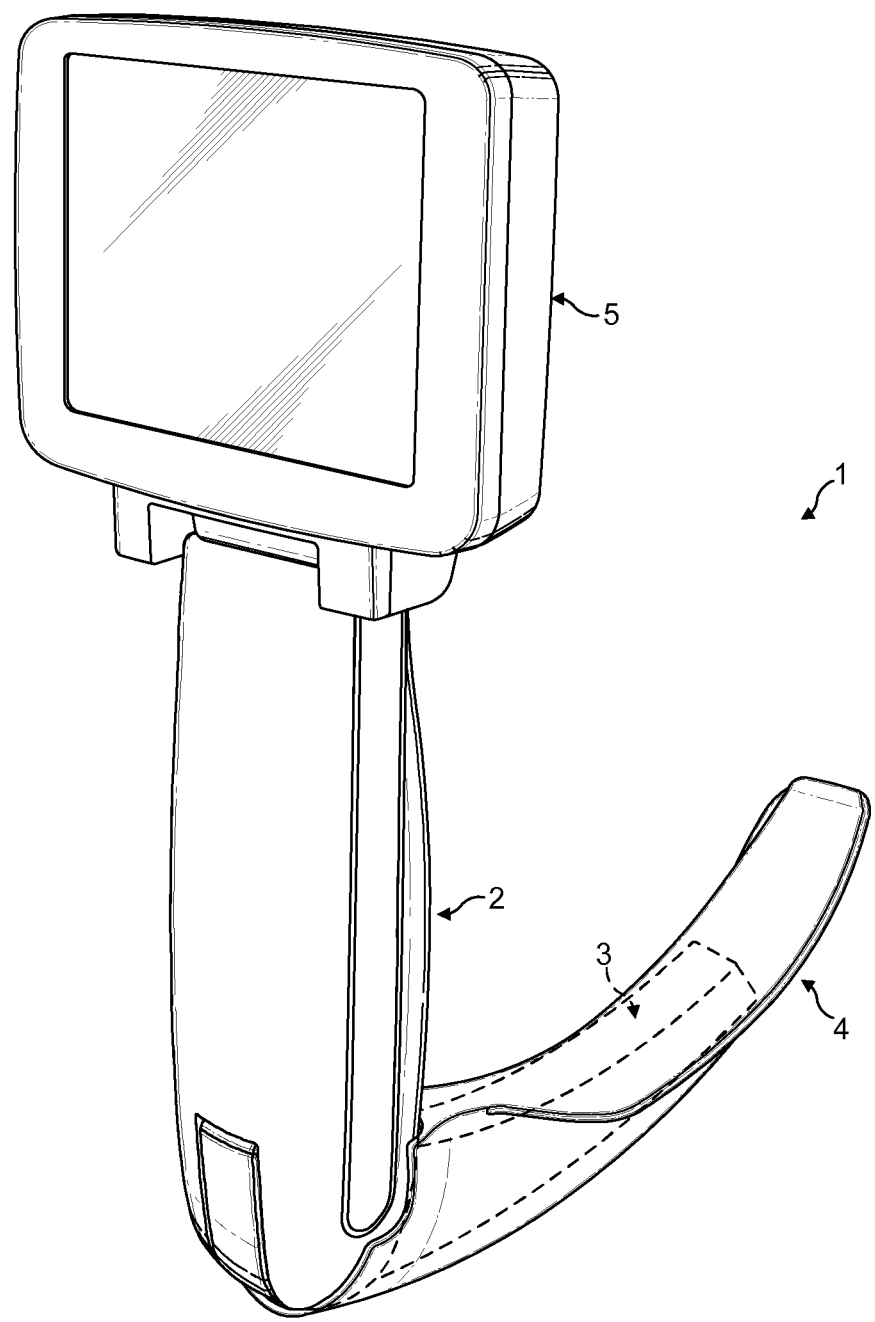
FIG. 1 is a perspective view of a laryngoscope according to an embodiment of the invention.

The laryngoscope (1) of FIG. 1 comprises a handle (2) for holding and manoeuvring the laryngoscope, a blade holding element (3) that is pivotally attached to the handle (2) and a blade (4) that is attached to the blade holding element (3). The laryngoscope (1) further comprises means of visualisation including a display screen (5) to visualise the area captured, for example, by a camera (not shown). This embodiment has a viewing means comprising a fibre optic viewing device but within the context of the invention, the viewing means may include any of a fibre optic device, camera, viewing screen and/or other viewing means. The laryngoscope may be used without a visualisation means such as camera, viewer and/or fibre optics for straightforward cases but the use of a visualisation means is recommended in more complex and difficult intubation situations.

The handle (2) is preferably made of stainless steel for robustness, although other materials such as metals or plastics may be used. In the embodiment of FIG. 1 a detachable display screen (5) is connected at the proximal end of the handle (2). At the proximal end, the blade holding element (3) is pivotally connected to the heel of the handle (2).

Figure 2:
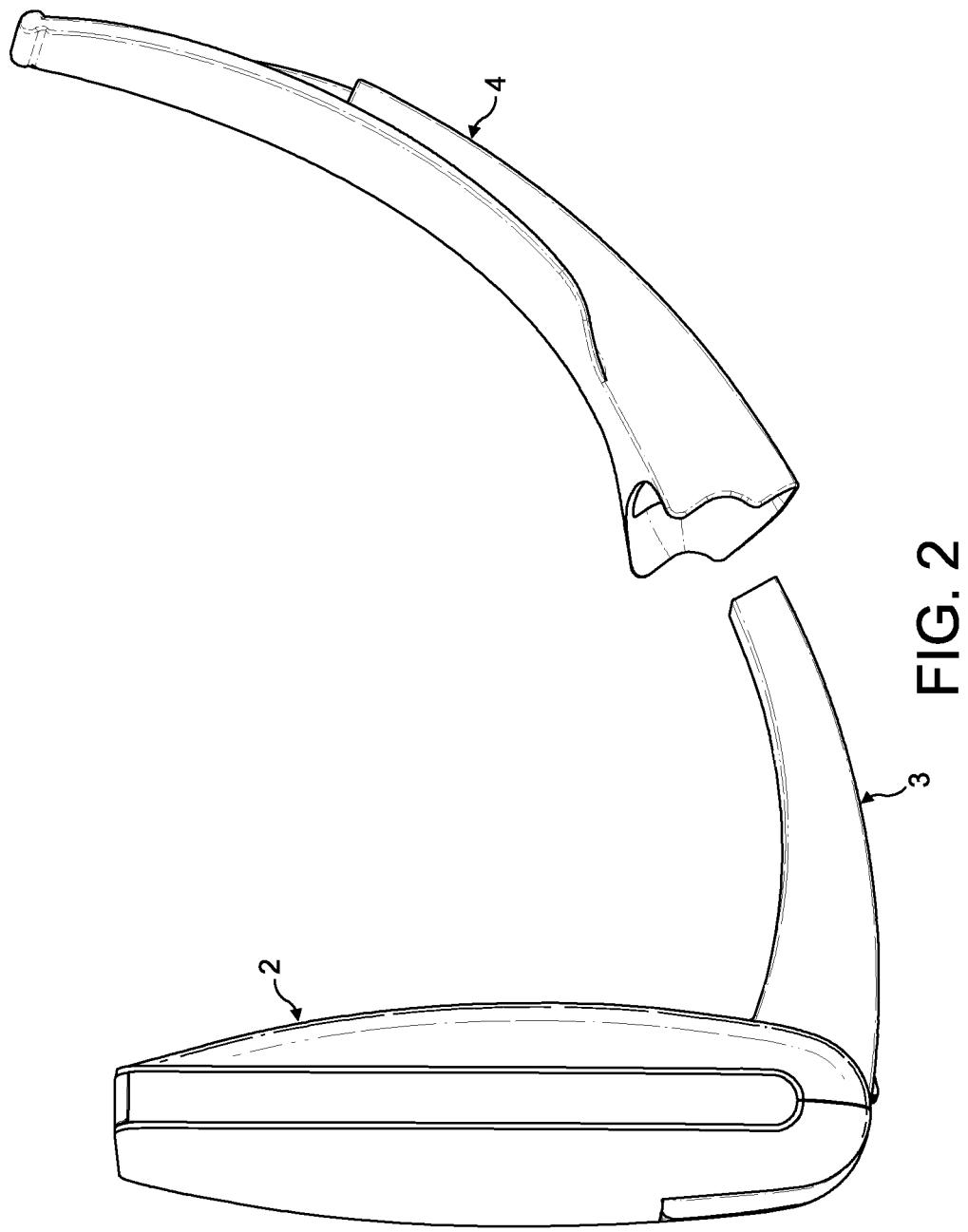
FIG. 2 is a side view of a laryngoscope according to an embodiment of the invention wherein the blade is detached.
Figure 3:
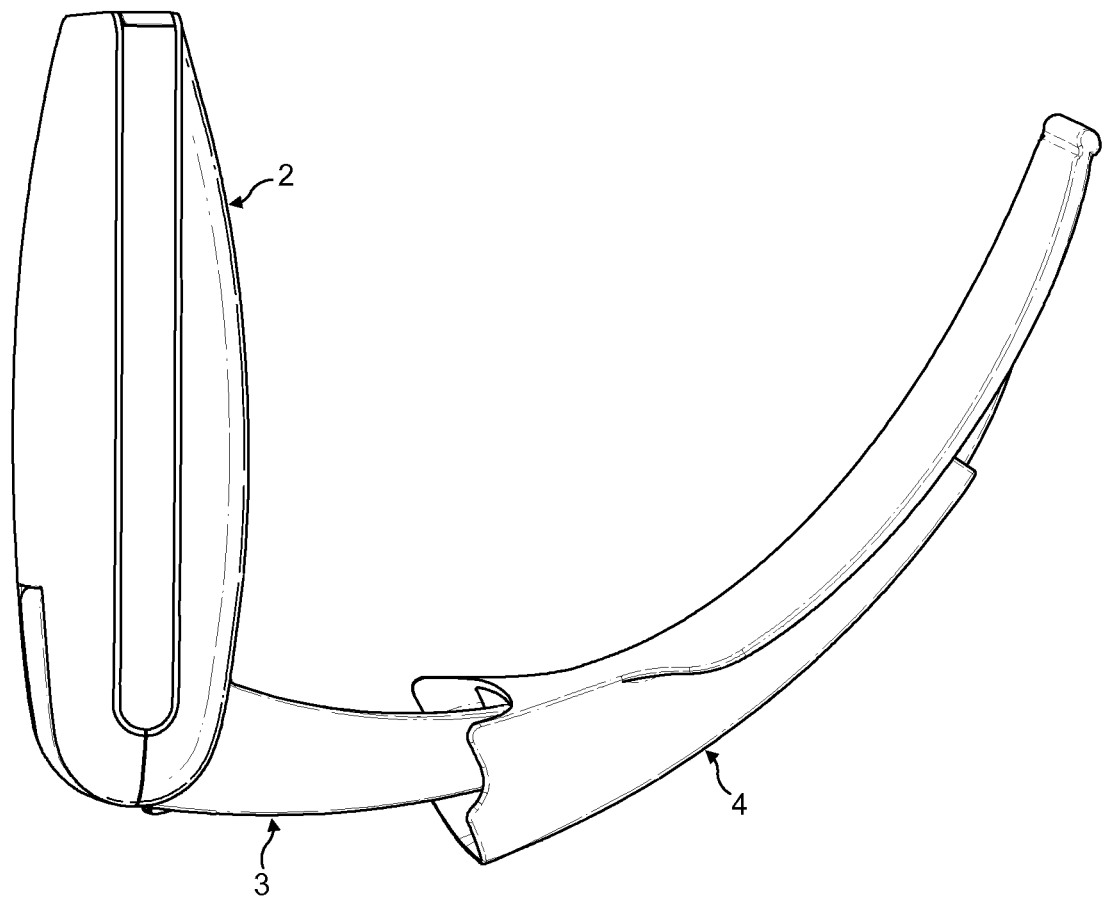
FIG. 3 is a side view of the laryngoscope of FIG. 2 wherein the blade is sliding onto the blade holding element.

The blade (4) may be hollow so that it can be fitted onto the blade holding element by sliding as can be seen in FIGS. 2 and 3 (described in more detail below). Preferably, the blade holding element (3) is elongated in shape and its outer contour corresponds substantially to the inner shape of the blade (4). In a preferred embodiment, the blade (4) may comprise a pair of wings (6) that fit the contour of the heel of the handle (2).

Figure 4:
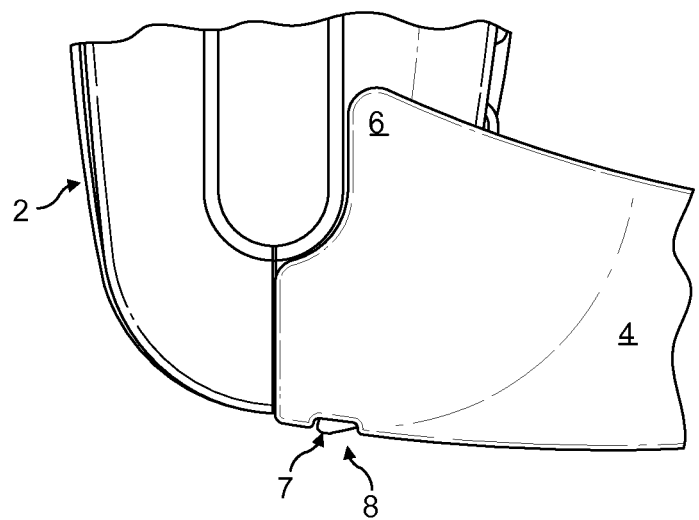
FIG. 4 is a partial side view of the laryngoscope of FIG. 2 showing a snap clip system used in the invention.

As can be seen in FIG. 4, the proximal end of the blade (4) is connected to the proximal end of the blade holding element (3) by means of a snap clip. In this embodiment, the blade holding element (3) comprises a tooth (7) that can snap into a corresponding groove (8) in the blade (4). It can be envisaged a construction in which the blade (4) comprises a tooth (7) and the blade holding element (2), the corresponding groove (8). The tooth (7) is shaped to allow the blade (4) to slide on easily, but prevent its accidental removal. Preferably, the height of the tooth (7) is less than the depth of the groove (8) so that there are substantially no protruding parts.

The blade (4) is preferably integrally constructed and is for example produced by injection moulding so that the cost of production is relatively affordable. However, two-part blades may also be used, where the components are joined together by welding, gluing or clipping. The blade is preferably disposable to minimise or eliminate any risk of cross-contamination between patients. Preferably the blade (4) is partially or wholly made of a flexible material, such as a flexible thermoplastic material. Most preferably, the blade wings (6) are made of a flexible material, such as a flexible thermoplastic material. Also, the blade or part of the blade may be flexible due to its shape, design or dimension (e.g. thickness).

The blade (4) may be straight, e.g. a Miller laryngoscope blade. Preferably, a curved blade may be used, e.g. a Macintosh blade, because a curved blade can be dimensioned to conform to the anatomical curve of the patient's throat.

The laryngoscope (1) may comprise a light source and/or visualisation means such as fibreoptics, camera, display screen or other technology that enable external indirect visualisation of the laryngeal inlet.

A light source may be provided so that the distal tip of the blade is illuminated. This can be achieved for example by providing the handle with electrical power, such as a battery supply, which is electrically connected to a light source preferably located at the distal end of the blade holding element so that light exits through an opening in the distal part of the blade (4). Alternatively, electrical power may be provided by the viewer where a viewer is provided.

Similarly, visualisation means may be provided to view the distal tip of the blade (4) and the laryngeal inlet. For example, a fibre optic viewing means may be mounted in the blade holding element and comprise optical fibres. The fibres may be arranged so that their proximal end is attached to a screen (5). The screen is preferably detachable so that the equipment can be easily cleaned after use. The fibres exit from the distal end of the blade holding element (3) and through an opening in the distal part of the blade (4) to view the laryngeal inlet. Alternatively, the material of the blade may be wholly or partly transparent so as to allow visualisation instead of using an opening which could be considered to be prone to contamination. In another preferred embodiment, a camera is located at the distal end of the blade holding element.

The blade (4) is attached to the blade holding element (3) by means of a snap clip (7,8). In this embodiment, and as can be seen on FIGS. 2 and 3, the blade holding element (3) is placed in the operative position (i.e. substantially perpendicular to the handle). The user can slide the hollow blade (4) onto the blade holding element (3)—in a direction from the distal end to the proximal end of the element (4). Preferably, the outer contour of the blade holding element (3) corresponds substantially to the inner shape of the blade (4) to minimise or eliminate any movement of blade (4) relative to the blade holding element (3) in use.

Figure 5:
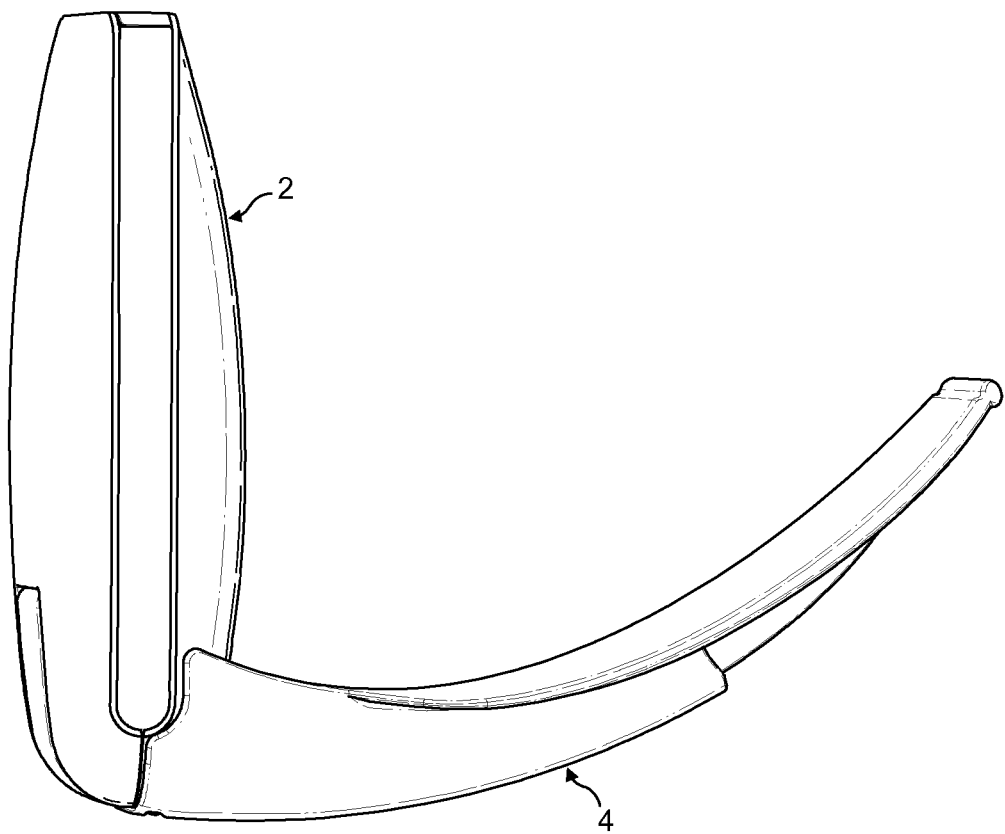
FIG. 5 is a side view of the laryngoscope of FIG. 2 wherein the blade is connected.
Figure 6:
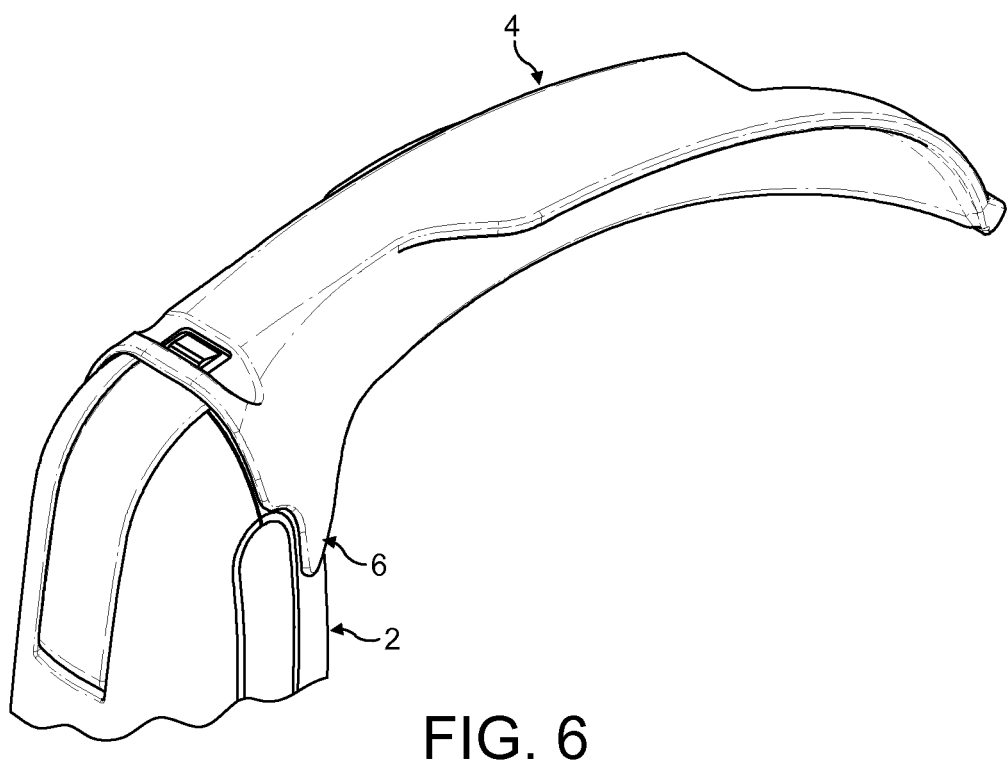
FIG. 6 is a partial perspective view of the laryngoscope of FIG. 2 wherein the blade is connected.

As can be seen in FIGS. 4 to 6, when the limit of travel is reached, the tooth (7) of the blade holding element (3) snaps into the groove (8) of the blade (4). A correct fit is indicated by audible feedback of the tooth (7) snapping into place. The blade (4) is held in place by a tooth (7) which is shaped to allow the blade (4) to slide on easily, but prevent its accidental removal.

Figure 7:
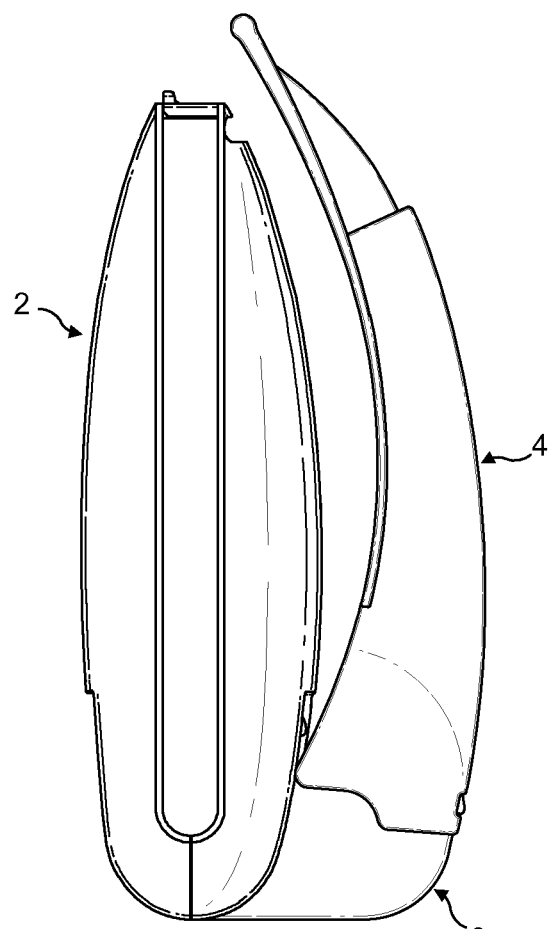
FIG. 7 is a side view of the laryngoscope of FIG. 2 in an inoperative position.

In this embodiment, the blade (4) is detached from the blade holding element (3) by setting the laryngoscope (1) to its inoperative position by folding up the blade holding element (3) as shown for example in FIG. 7.

Figure 8:
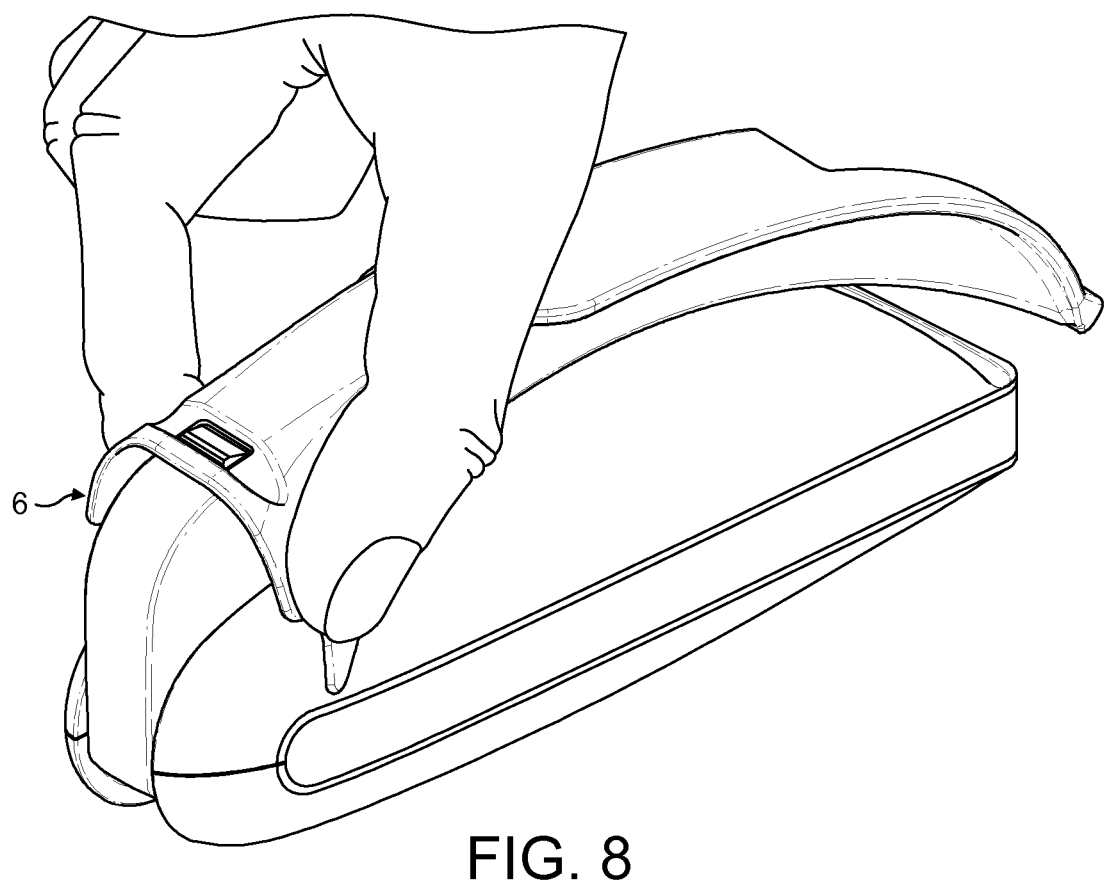
FIGS. 8 and 9 are perspective views of the laryngoscope of FIG. 2 wherein the blade is being detached from the blade holding element.
Figure 9:
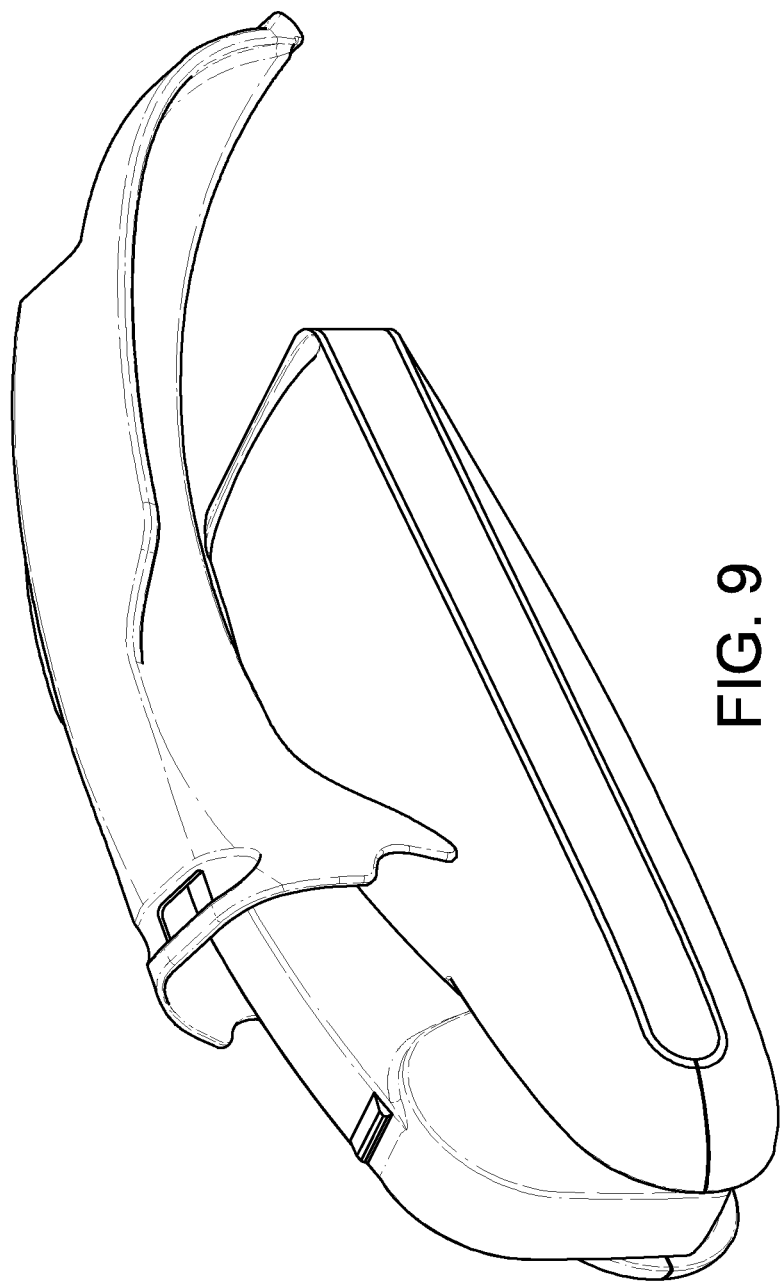

As can be seen in FIG. 8, the blade (4) may be removed by applying pressure onto the blade wings (6). The flexibility of the wings material deforms the area around the tooth catch (7), sending it away from the blade holding element and allowing the blade to clear the tooth (7) and slide away from it. The fit between the blade (4) and the heel of the handle (2) prevents the blade (4) from being removed whilst the laryngoscope (1) is in use since it is difficult to deform the blade (4) by pinching because of the presence of the handle (2).

In operation, the laryngoscope (1) is inserted into the mouth of the patient. The blade (4) will push the tongue of the patient to the side of the oropharynx to create space through which the larynx and the epiglottis can be viewed. The blade (4) is manipulated to lift the epiglottis thereby exposing the laryngeal inlet. An endotracheal tube can then be introduced and advanced past the vocal cords into the trachea. The user can visualise the distal end of the blade (4) for example on the display screen and manipulate the laryngoscope (1) accordingly. Once the tube is correctly positioned, the laryngoscope (1) is removed.

The invention claimed is:

1. A laryngoscope comprising a handle, a releasable blade, a blade holding element and releasable attachment means to attach the blade to the blade holding element; wherein the blade holding element is pivotally attached to the handle, so that the blade may be arranged in a first operative position and a second inoperative position and the attachment means is releasable when the blade is in the second inoperative position.

2. The laryngoscope according to claim 1 wherein the blade and the blade holding element comprise mutually cooperative releasable attachment means.

3. The laryngoscope according to claim 2 wherein at least one of the releasable attachment means comprises a resiliency deformable element.

4. The laryngoscope according to claim 2 wherein the releasable attachment means is a snap clip system.

5. The laryngoscope according to claim 4 wherein the snap clip means comprises at least one tooth and a corresponding groove for receiving the tooth.

6. The laryngoscope according to claim 5, wherein the blade holding element comprises a tooth and the blade comprises a corresponding groove.

7. The laryngoscope according to claim 5, wherein the blade comprises a tooth and the blade holding element comprises a corresponding groove.

8. The laryngoscope according to claim 1, wherein the blade is slidable onto the blade holding element.

9. The laryngoscope according to claim 8, wherein the blade covers the blade holding element.

10. The laryngoscope according to claim 1, wherein the blade is shaped so that it is not detachable when in the first operative position.

11. The laryngoscope according to claim 1, wherein the blade is made partially or wholly of a flexible thermoplastic material.

12. The laryngoscope according to claim 1, wherein the laryngoscope further comprises a light source.

13. The laryngoscope according to claim 1, wherein the laryngoscope further comprises vizualisation means.

14. A blade for use with a laryngoscope according to claim 1.

15. A handle for use with a laryngoscope according to claim 1.

16. The laryngoscope according to claim 1, wherein pressure applied to the blade in the location of the attachment means in the inoperative position causes deformation of the blade and release of the attachment means.

17. The laryngoscope according to claim 16, wherein the handle has a distal end and a proximal end and the fit between the blade and the proximal end of the handle in the operative position prevents the blade from being deformed and released.

18. A laryngoscope comprising a handle, a blade holding element having a proximal end pivotally attached to the handle and being movable between a first operative position and a second inoperative position, the blade holding element comprising a resiliency deformable tooth proximate the proximal end thereof, and a blade slidable onto the blade holding element and comprising a deformable groove arranged proximate a proximal end thereof to engage the resiliency deformable tooth when the blade has reached its limit of travel on the blade holding element and to hold the blade in place.

19. The laryngoscope according to claim 18, wherein pressure applied to the blade proximate the proximal end thereof in the inoperative position causes deformation of the blade and release of the blade.

20. The laryngoscope according to claim 18, wherein the handle has a distal end and a proximal end and the fit between the blade and the proximal end of the handle in the operative position prevents the blade from being deformed and released.

21. The laryngoscope according to claim 18, wherein the blade covers the blade holding element.

* * * * *